United States Patent
Hodde

(10) Patent No.: US 9,138,445 B2
(45) Date of Patent: Sep. 22, 2015

(54) MEDICAL GRAFT MATERIALS WITH ADHERENT EXTRACELLULAR MATRIX FIBROUS MASS

(75) Inventor: Jason P. Hodde, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 377 days.

(21) Appl. No.: 11/372,158

(22) Filed: Mar. 9, 2006

(65) Prior Publication Data

US 2006/0201996 A1 Sep. 14, 2006

Related U.S. Application Data

(60) Provisional application No. 60/660,015, filed on Mar. 9, 2005.

(51) Int. Cl.
| | | |
|---|---|---|
| A61K 35/12 | (2015.01) | |
| A61K 35/38 | (2015.01) | |
| A61K 35/24 | (2015.01) | |
| A61K 38/18 | (2006.01) | |
| A61L 27/34 | (2006.01) | |
| A61L 27/36 | (2006.01) | |
| A61L 27/52 | (2006.01) | |

(52) U.S. Cl.
CPC .............. *A61K 35/24* (2013.01); *A61K 35/38* (2013.01); *A61K 38/1825* (2013.01); *A61L 27/34* (2013.01); *A61L 27/3629* (2013.01); *A61L 27/3633* (2013.01); *A61L 27/52* (2013.01)

(58) Field of Classification Search
USPC .................................. 424/550, 520, 572, 482
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,275,826 A * | 1/1994 | Badylak et al. | 424/551 |
| 5,281,422 A | 1/1994 | Badylak et al. | |
| 5,460,939 A | 10/1995 | Hansbrough et al. | |
| 5,512,475 A | 4/1996 | Naughton et al. | |
| 5,554,389 A | 9/1996 | Badylak et al. | |
| 5,893,888 A | 4/1999 | Bell | |
| 5,948,429 A | 9/1999 | Bell et al. | |
| 5,955,110 A | 9/1999 | Patel et al. | |
| 5,993,844 A | 11/1999 | Abraham et al. | |
| 6,099,567 A | 8/2000 | Badylak et al. | |
| 6,153,292 A | 11/2000 | Bell et al. | |
| 6,179,872 B1 | 1/2001 | Bell et al. | |
| 6,206,931 B1 * | 3/2001 | Cook et al. | 623/23.75 |
| 6,375,989 B1 * | 4/2002 | Badylak et al. | 424/551 |
| 6,475,232 B1 | 11/2002 | Babbs et al. | |
| 6,559,119 B1 * | 5/2003 | Burgess et al. | 514/2 |
| 6,821,107 B1 | 11/2004 | Hara et al. | |
| 7,041,505 B2 * | 5/2006 | Tsuzuki et al. | 435/401 |
| 2002/0009805 A1 | 1/2002 | Nevo et al. | |
| 2002/0099448 A1 | 7/2002 | Hiles et al. | |
| 2002/0183858 A1 | 12/2002 | Contiliano et al. | |
| 2003/0013989 A1 | 1/2003 | Obermiller et al. | |
| 2003/0023316 A1 | 1/2003 | Brown et al. | |
| 2003/0049299 A1 | 3/2003 | Malaviya et al. | |
| 2003/0133967 A1 | 7/2003 | Ruszczak et al. | |
| 2003/0167088 A1 * | 9/2003 | Abraham et al. | 623/1.41 |
| 2004/0059431 A1 | 3/2004 | Plouhar et al. | |
| 2004/0078090 A1 | 4/2004 | Binette et al. | |
| 2004/0166169 A1 | 8/2004 | Malaviya et al. | |
| 2005/0021141 A1 * | 1/2005 | Bleyer et al. | 623/15.12 |
| 2005/0187604 A1 | 8/2005 | Eells et al. | |
| 2005/0249772 A1 | 11/2005 | Malaviya et al. | |
| 2005/0283255 A1 | 12/2005 | Geremakis et al. | |
| 2007/0184122 A1 * | 8/2007 | Johnson et al. | 424/550 |

FOREIGN PATENT DOCUMENTS

| | | | |
|---|---|---|---|
| WO | WO 03/002165 | 1/2003 | |
| WO | WO/03002165 | 1/2003 | |
| WO | WO 03/035125 | * 5/2005 | |

OTHER PUBLICATIONS

Hiles et al., Tissue engineering a clinically useful extracellular matrix biomaterialInternational Urogynecology Journal, 2006, pp. S39-S43.*

* cited by examiner

*Primary Examiner* — Maria Leavitt
(74) *Attorney, Agent, or Firm* — Woodard Emhardt Moriarty McNett & Henry LLP

(57) ABSTRACT

Described are medical grafting materials that include a base substrate material and an adherent fibrous mass of extracellular matrix components received upon the substrate material. Also described are methods of preparing and using such materials.

13 Claims, 1 Drawing Sheet

MEDICAL GRAFT MATERIALS WITH ADHERENT EXTRACELLULAR MATRIX FIBROUS MASS

The present application claims the benefit of U.S. Provisional Patent Application Ser. No. 60/660,015 filed Mar. 9, 2005 entitled "MEDICAL GRAFTS MATERIALS WITH ADHERENT EXTRACELLULAR MATRIX FIBROUS MASS" which is hereby incorporated by reference in its entirety.

BACKGROUND OF THE INVENTION

The present invention relates generally to medical materials, and in one particular aspect to medical graft materials that include a substrate and an adherent mass of fibrils derived from an extracellular matrix material received thereon.

As further background, a variety of medical graft materials have been disclosed for use in medical applications, including those in human and in animals (veterinary medical applications). Included among these tissue graft materials are extracellular matrix (ECM) materials that are derived from animal tissue sources. These ECM materials include, for example, submucosal and other ECM materials.

While such medical graft materials have been generally disclosed, needs remain for improved and alternative graft materials that include varied structural, functional and/or biochemical features rendering them improved or suitable for one or a variety of medical applications. The present invention is addressed to these needs.

SUMMARY OF THE INVENTION

Accordingly, in one aspect, the present invention provides a method for preparing an extracellular matrix graft material. The method includes providing a biocompatible substrate layer, and applying a flowable composition to the substrate layer, wherein the flowable composition includes solubilized extracellular matrix components. The flowable composition is dried to form a layer including a deposited extracellular matrix fibrous mass, including in certain embodiments of the invention a generally random deposit of collagen fibers. The biocompatible substrate layer can comprise a remodelable extracellular matrix sheet material, such as, for example, submucosa. As well, embodiments of the invention are provided wherein the applied flowable composition includes particulate collagenous extracellular matrix components.

In another embodiment, the present invention provides a medical graft material that includes a biocompatible substrate layer and adhered thereto a fibrous mass or cake of extracellular matrix components, desirably provided as a coherent layer. In desired embodiments, the fibrous mass of extracellular matrix materials includes a generally random distribution of collagen fibers and retains bioactive components such as one or more growth factors. Thus, the extracellular matrix mass or cake can exhibit biotropic properties, including for example demonstrating an angiogenic character.

Additional embodiments of the invention relate to methods for using graft materials as described herein.

Still further embodiments as well as features and advantages of the invention will be apparent to one of ordinary skill in the art from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

Figure 1:
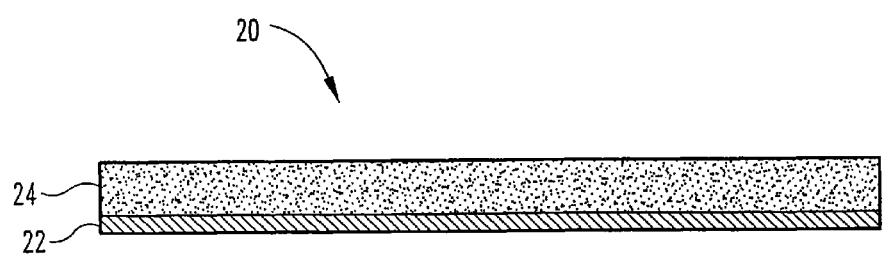
FIG. 1 provides a cross-section view of an illustrative medical graft material of the invention.

As disclosed above the present invention provides medical graft materials and methods for their preparation and use. With reference to FIG. 1, in certain aspects, a medical graft material 20 of the invention includes a biocompatible base substrate 22, and an adherent fibrous mass 24 derived from an extracellular matrix material.

A wide variety of biocompatible base substrate materials are useful for purposes of the invention. For example, these include sheet or other substrate materials comprised of biopolymers such as collagen or gelatin, as well as sheet or other substrate materials made from synthetic polymers, resorbable and/or non-resorbable. Substrate materials made with combinations of biopolymers and synthetic polymers are also suitable for use in the invention. In certain inventive aspects, the substrate material will be bioresorbable.

In advantageous aspects, both the biocompatible substrate material and the adherent fibrillar mass or cake will be provided by an extracellular matrix (ECM) material. Suitable bioremodelable materials can be provided by collagenous extracellular matrix materials (ECMs) possessing biotropic properties, including in certain forms angiogenic collagenous extracellular matrix materials. In this regard, suitable ECM materials for use in the invention include naturally-derived collagenous ECMs isolated from suitable animal or human tissue sources. Suitable such extracellular matrix materials include, for instance, submucosa (including for example small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials, or other collagenous layers derived from these or other organ sources. These materials may be isolated and used as intact natural sheet forms, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567. Renal capsule membrane can also be obtained from warm-blooded vertebrates, as described more particularly in International Patent Application Ser. No. PCT/US02/20499 filed Jun. 28, 2002, published Jan. 9, 2003 as WO03002165.

Preferred ECM base materials for use in the invention (both to provide the substrate and to prepare the flowable ECM composition) contain residual bioactive proteins or other ECM components derived from the tissue source of the materials. For example, they may contain Fibroblast Growth Factor-2 (basic FGF), Transforming Growth Factor-beta (TGF-beta), vascular endothelial growth factor (VEGF), epidermal growth factor (EGF) and/or platelet derived growth factor (PDGF). It is also expected that ECM base materials of the invention may contain additional bioactive components including, for example, one or more of glycosaminoglycans, glycoproteins, proteoglycans, and/or growth factors. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

The formation of the deposited or adherent extracellular matrix fibrous mass or cake can be achieved in any suitable manner. In one preferred approach, a liquid or otherwise flowable composition comprising solubilized extracellular matrix components (e.g. including solubilized collagen) is applied to the substrate, and then dried to form the cake or mass layer.

For these purposes, the liquid or flowable composition including solubilized extracellular matrix components can be prepared at follows. An isolated ECM material can be used to prepare a solubilized mixture including components of the material. This can be achieved by digestion of the ECM material in an acidic or basic medium and/or by contact with an appropriate enzyme or combination of enzymes.

For example, in an illustrative preparative embodiment, the fibrous mass layer forming material can be made by first reducing ECM material to particulate form to aid in a digestion step. This can be achieved by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in an industrial blender.

Next, the particulate ECM material can be subjected to digestion using any suitable enzyme in an enzymatic digestion step. Such enzymes include for example serine proteases, aspartyl proteases, and matrix metalloproteases. The concentration of the enzyme can be adjusted based on the specific enzyme used, the amount of ECM to be digested, the duration of the digestion, the temperature of the reaction, and the desired properties of the remodelable fibril mass layer forming material. In an illustrative embodiment, about 0.1% to about 0.2% of enzyme (pepsin, for example) can be used and the digestion can be conducted under cooled conditions for a period of time sufficient to substantially digest the ECM material. The digestion can be conducted at any suitable temperature, with temperatures ranging from 4° to 37° C. being preferred. Likewise, any suitable duration of digestion can be used, such durations typically falling in the range of about 2 to 180 hours. The ratio of the concentration of ECM material (hydrated) to total enzyme usually ranges from about 25 to about 125 and more typically the ratio is about 50, and the digestion is conducted at approximately 4° C. for approximately 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2 to 4.

If necessary or desired, the enzymes or other disruptive agents used to solubilize the ECM material can be removed or inactivated before proceeding with the formation of the mass layer. Also, any disruptive agent, particularly enzymes, that remains present and active during storage of the tissue can potentially change the composition and potentially the layer forming characteristics of the solution. Enzymes, such as pepsin, can be inactivated with protease inhibitors, a shift to neutral pH, a drop in temperature below 0° C., heat inactivation, or through the removal of the enzyme by fractionation. A combination of these methods can be utilized to stop digestion of the ECM material at a predetermined endpoint, for example the ECM material can be immediately frozen and later fractionated to limit digestion.

Illustratively, during preparation of a suitable fibrous mass layer forming material, the ECM material can be enzymatically digested for a sufficient time to produce a hydrolysate of ECM components. Accordingly, the ECM can be treated with one enzyme or with a mixture of enzymes to hydrolyze the structural components of the material and prepare a hydrolysate having multiple hydrolyzed components of reduced molecular weight. The length of digestion time can be varied depending on the application, and the digestion can be extended to completely solubilize the ECM material. In some modes of operation, the ECM material will be treated sufficiently to partially solubilize the material to produce a digest composition comprising hydrolyzed ECM components and nonhydrolyzed ECM components. The digest composition can then, in illustrative embodiments, be further processed to remove at least some of the nonhydrolyzed components. For example, the nonhydrolyzed components can be separated from the hydrolyzed portions by centrifugation, filtration, or other separation techniques known in the art.

Illustratively, preferred gel-form fibrous mass layer forming materials can be prepared from enzymatically digested vertebrate ECM material that has been fractionated under acidic conditions, for example including pH ranging from about 2 to less than 7, especially to remove low molecular weight components. Typically, the ECM hydrolysate is fractionated by dialysis against a solution or other aqueous medium having an acidic pH, e.g. a pH ranging from about 2 to about 7. In addition to fractionating the hydrolysate under acidic conditions, the ECM hydrolysate is typically fractionated under conditions of low ionic strength with minimal concentrations of salts such as those usually found in standard buffers such as PBS (i.e. NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

The hydrolysate solution produced by enzymatic digestion of the ECM material has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested ECM tissue. For example, digestion of vertebrate ECM material with a protease such as pepsin, followed by dialysis, will form a fractionated ECM hydrolysate having a lower protein to carbohydrate ratio relative to the original ECM material.

Flowable ECM compositions capable of forming shape retaining gels can be used as fibrous mass layer forming material in the present invention. Illustrative such ECM compositions can be prepared from ECM material that has been enzymatically digested and fractionated under acidic conditions to form an ECM hydrolysate that has a protein to carbohydrate ratio different than that of the original ECM material. Such fractionation can be achieved entirely or at least in part by dialysis. The molecular weight cut off of the ECM components to be included in the gellable material is selected based on the desired properties of the gel. Typically the molecular weight cutoff of the dialysis membrane (the molecular weight above which the membrane will prevent passage of molecules) is within in the range of about 2000 to about 10000 Dalton, and more preferably from about 3500 to about 5000 Dalton.

In certain forms of the ECM mass layer forming material composition, apart from the potential removal of undigested ECM components after the digestion step and any controlled fractionation to remove low molecular weight components as discussed above, the ECM hydrolysate is processed so as to avoid any substantial further physical separation of the ECM components. For example, when a more concentrated ECM hydrolysate material is desired, this can be accomplished by removing water from the system (e.g. by evaporation or lyophilization) as opposed to using conventional "salting out"/centrifugation techniques that would demonstrate significant selectivity in precipitating and isolating collagen, leaving behind amounts of other desired ECM components. Thus, in certain embodiments of the invention, solubilized ECM components of the ECM hydrolysate remain substantially unfractionated, or remain substantially unfractionated above a predetermined molecular weight cutoff such as that used in the dialysis membrane, e.g. above a given value in the range of about 2000 to 10000 Dalton, more preferably about 3500 to about 5000 Dalton.

In the manufacture of suitable fibrous mass layer forming material, vertebrate ECM material can be stored frozen (e.g. at about −20 to about −80° C.) in either its solid, comminuted or enzymatically digested forms, or the material can be stored after being hydrolyzed and fractionated. The ECM material can be stored in solvents that maintain the collagen in its native form and solubility. For example, one suitable storage solvent is 0.01 M acetic acid, however other acids can be substituted, such as 0.01 N HCl. In one form, the fractionated ECM hydrolysate can be dried (by lyophilization, for example) and stored in a dehydrated/lyophilized state. The dried form can be rehydrated to prepare a flowable ECM composition capable of forming a gel that can be used as a fibril mass layer forming material in the present invention.

In accordance with an illustrative method of fibril mass layer forming material preparation, the fractionated ECM hydrolysate or other flowable ECM composition will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate can be adjusted by the addition of a buffer that does not leave a toxic residue, and has a physiological ion concentration and the capacity to hold physiological pH. Examples of suitable buffers include PBS, HEPES, and DMEM. Illustratively, the pH of the fractionated ECM hydrolysate can be raised by the addition of a buffered NaOH solution to 6.6 to 8.0, more preferably 7.2 to 7.8, to facilitate the formation of an ECM-containing gel. Any suitable concentration of NaOH solution can be used for these purposes, for example including about 0.05 M to about 0.5 M NaOH. In accordance with an embodiment, the ECM hydrolysate is mixed with a buffer and sufficient 0.25 N NaOH is added to the mixture to achieve the desired pH.

The ionic strength of the ECM hydrolysate is believed to be important in maintaining the fibers of collagen in a state that allows for fibrillogenesis and matrix gel assembly upon neutralization of the hydrolysate. Accordingly, if needed, the salt concentration of the ECM hydrolysate material can be reduced prior to neutralization of the hydrolysate. The neutralized hydrolysate can be caused to gel at any suitable temperature, e.g. ranging from about 4° C. to about 40° C. The temperature will typically affect the gelling times, which may range from about 5 to about 120 minutes at the higher gellation temperatures and about 1 to about 8 hours at the lower gellation temperatures. Typically, the hydrolysate will be effective to self-gel at elevated temperatures, for example at about 37° C. In this regard, preferred neutralized ECM hydrolysates will be effective to gel in less than about ninety minutes at 37° C., for example within about 30 seconds to thirty minutes at 37° C.

In alternative embodiments, additional components can be added to the ECM hydrolysate composition before, during, or after forming the fibrous mass layer. For example, proteins carbohydrates, growth factors, as discussed above, therapeutics, bioactive agents, nucleic acids, cells or pharmaceuticals can be added. In certain embodiments, such materials are added prior to formation of the fibril mass layer. This may be accomplished for example by forming a dry mixture of a powdered ECM hydrolysate with the additional component(s), and then reconstituting and gelling the mixture, or by incorporating the additional component(s) into an aqueous, ungelled composition of the ECM hydrolysate before, during (e.g. with) or after addition of the neutralization agent. The additional component(s) can also be added to a formed ECM gel, e.g. by infusing or mixing the component(s) into the gel and/or coating them onto the gel. In certain embodiments, the gel can then be dried (e.g. by lyophilization).

In one illustrative fibrous mass layer forming material preparation, a particulate ECM material can be added to an ECM hydrolysate composition, which can then be incorporated in a formed gel and ultimately in a dried mass. Such particulate ECM materials can be prepared by cutting, tearing, grinding or otherwise comminuting an ECM starting material. For example, a particulate ECM material having an average particle size of about 50 microns to about 500 microns may be included in the gellable ECM hydrolysate, more preferably about 100 microns to about 400 microns. The ECM particulate can be added in any suitable amount relative to the hydrolysate, with preferred ECM particulate to ECM hydrolysate weight ratios (based on dry solids) being about 0.1:1 to about 200:1, more preferably in the range of about 1:1 to about 100:1. The inclusion of such ECM particulates in the ultimate gel or fibril mass layer forming material can serve to provide additional material that can function to provide bioactivity to the gel (e.g. itself including FGF-2 and/or other growth factors or bioactive substances as discussed herein) and/or serve as scaffolding material for tissue ingrowth.

In certain embodiments, flowable ECM compositions to be used as fibrous mass layer forming material in the invention may be disinfected by contacting an aqueous medium including ECM hydrolysate components with an oxidizing disinfectant. This mode of disinfection provides an improved ability to recover a disinfected ECM hydrolysate that exhibits the capacity to form beneficial gels. In certain preparative methods, an aqueous medium containing ECM hydrolysate components can be disinfected by providing a peroxy disinfectant in the aqueous medium. This can be advantageously achieved using dialysis to deliver the peroxy disinfectant into and/or to remove the peroxy disinfectant from the aqueous medium containing the hydrolysate. In certain disinfection techniques, an aqueous medium containing the ECM hydrolysate is dialyzed against an aqueous medium containing the peroxy disinfectant to deliver the disinfectant into contact with the ECM hydrolysate, and then is dialyzed against an appropriate aqueous medium (e.g. an acidic aqueous medium) to at least substantially remove the peroxy disinfectant from the ECM hydrolysate. During this dialysis step, the peroxy compound passes through the dialysis membrane and into the ECM hydrolysate, and contacts ECM components for a sufficient period of time to disinfect the ECM components of the hydrolysate. In this regard, typical contact times will range from about 0.5 hours to about 8 hours and more typically from about 1 hour to about 4 hours. The period of contact will be sufficient to substantially disinfect the digest, including the removal of endotoxins and inactivation of virus material present. The removal of the peroxy disinfectant by dialysis may likewise be conducted over any suitable period of time, for example having a duration of about 4 to about 180 hours, more typically of about 24 to about 96 hours. In general, the disinfection step will desirably result in a disinfected ECM hydrolysate composition having sufficiently low levels of endotoxins, viral burdens, and other contaminant materials to render it suitable for use as a fibril mass layer forming material. Endotoxin levels below about 2 endotoxin units (EUs) per gram (dry weight) are preferred, more preferably below about 1 EU per gram, as are virus levels below 100 plaque forming units per gram (dry weight), more preferably below 1 plaque forming unit per gram.

The aqueous ECM hydrolysate composition can be a substantially homogeneous solution during the dialysis step for delivering the oxidizing disinfectant to the hydrolysate composition and/or during the dialysis step for removing the oxidizing disinfectant from the hydrolysate composition. Alternatively, the aqueous hydrolysate composition can include suspended ECM hydrolysate particles, optionally in combination with some dissolved ECM hydrolysate components, during either or both of the oxidizing disinfectant delivery and removal steps. Dialysis processes in which at least some of the ECM hydrolysate components are dissolved during the disinfectant delivery and/or removal steps are preferred and those in which substantially all of the ECM hydrolysate components are dissolved are more preferred.

The disinfection step can be conducted at any suitable temperature, and will typically be conducted between about 0° C. and about 37° C., more typically between about 4° C. and about 15° C. During this step, the concentration of the ECM hydrolysate solids in the aqueous medium can be in the range of about 2 mg/ml to about 200 mg/ml, and may vary somewhat through the course of the dialysis due to the migration of water through the membrane. In certain embodiments, a relatively unconcentrated digest is used, having a starting ECM solids level of about 5 mg/ml to about 15 mg/ml. In other embodiments, a relatively concentrated ECM hydrolysate is used at the start of the disinfection step, for example having a concentration of at least about 20 mg/ml and up to about 200 mg/ml, more preferably at least about 100 mg/ml and up to about 200 mg/ml. It has been found that the use of concentrated ECM hydrolysates during this disinfection processing results in an ultimate gel composition having higher gel strength than that obtained using similar processing with a lower concentration ECM hydrolysate. Accordingly, processes which involve the removal of amounts of water from the ECM hydrolysate resulting from the digestion prior to the disinfection processing step are preferred. For example, such processes may include removing only a portion of the water (e.g. about 10% to about 98% by weight of the water present) prior to the dialysis/disinfection step, or may include rendering the digest to a solid by drying the material by lyophilization or otherwise, reconstituting the dried material in an aqueous medium, and then treating that aqueous medium with the dialysis/disinfection step.

In an illustrative fibrous mass layer forming material preparation embodiment, the disinfection of the aqueous medium containing the ECM hydrolysate can include adding the peroxy compound or other oxidizing disinfectant directly to the ECM hydrolysate, for example being included in an aqueous medium used to reconstitute a dried ECM hydrolysate or being added directly to an aqueous ECM hydrolysate composition. The disinfectant can then be allowed to contact the ECM hydrolysate for a sufficient period of time under suitable conditions (e.g. as described above) to disinfect the hydrolysate, and then removed from contact with the hydrolysate. In one embodiment, the oxidizing disinfectant can then be removed using a dialysis procedure as discussed above. In other embodiments, the disinfectant can be partially or completely removed using other techniques such as chromatographic or ion exchange techniques, or can be partially or completely decomposed to physiologically acceptable components. For example, when using an oxidizing disinfectant containing hydrogen peroxide (e.g. hydrogen peroxide alone or a peracid such as peracetic acid), hydrogen peroxide can be allowed or caused to decompose to water and oxygen, for example in some embodiments including the use of agents that promote the decomposition such as thermal energy or ionizing radiation, e.g. ultraviolet radiation.

In an alternative fibrous mass layer forming material preparation, the oxidizing disinfectant can be delivered into the aqueous medium containing the ECM hydrolysate by dialysis and processed sufficiently to disinfect the hydrolysate (e.g. as described above), and then removed using other techniques such as chromatographic or ion exchange techniques in whole or in part, or allowed or caused to decompose in whole or in part as discussed immediately above.

Peroxygen compounds that may be used in the disinfection step include, for example, hydrogen peroxide, organic peroxy compounds, and preferably peracids. Such disinfecting agents are used in a liquid medium, preferably a solution, having a pH of about 1.5 to about 10.0, more desirably of about 2.0 to about 6.0. As to peracid compounds that can be used, these include peracetic acid, perpropioic acid, and/or perbenzoic acid. Peracetic acid is the most preferred disinfecting agent for purposes of the present invention.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol. For additional information concerning preferred peroxy disinfecting agents useful in certain disinfecting embodiments of the present invention, reference can be made, for example, to U.S. Pat. No. 6,206,931.

In certain embodiments, flowable, ECM-based fibrous mass layer forming materials of the present invention can be prepared to have desirable properties for manufacturing, handling and use. For example, fluidized ECM hydrolysates can be prepared in an aqueous medium, which can thereafter be effective to provide a fibril mass layer forming material. Such prepared aqueous mediums can have any suitable level of ECM hydrolysate therein. Typically, the ECM hydrolysate will be present in the aqueous medium at a concentration of about 1 mg/ml to about 200 mg/ml, more typically about 2 to about 120 mg/ml. Furthermore, flowable ECM compositions can be prepared so that in addition to neutralization, heating to physiologic temperatures (such as 37° C.) will substantially reduce the gelling time of the material.

Figure 2:
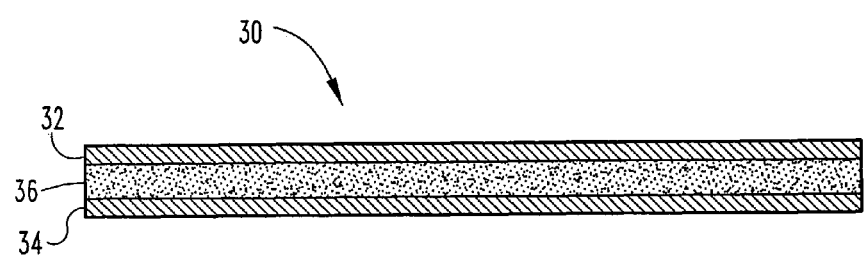
FIG. 2 provides a cross-sectional view of another illustrative medical graft material of the invention.
Figure 3:
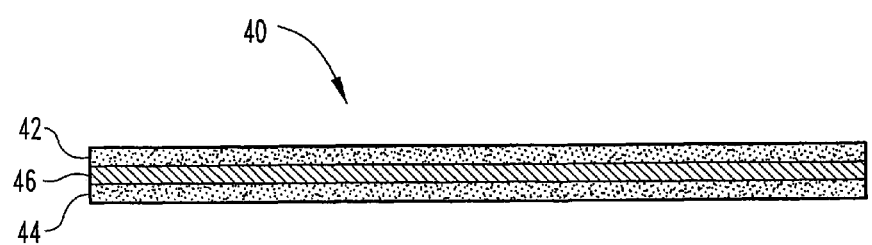
FIG. 3 provides a cross-sectional view of another illustrative medical graft material of the invention.

In the formation of medical graft materials of the invention, the liquid or otherwise flowable composition containing solubilized ECM components can be applied to the substrate material in any suitable fashion. For example, an amount of an ECM or other base sheet material can be spread, potentially within a mold, cast, or other structure for retaining and/or shaping the liquid composition to be applied. The flowable composition can then be added to the surface of the ECM or other base sheet material to a desired thickness or depth. In certain embodiments as discussed above, the flowable composition will be capable of forming a gel. This gel or other liquid-containing composition can then be dried to form a dried cake or mass that includes fibrous collagen derived from the ECM material, desirably along with one or more bioactive components native to the ECM material, as discussed above. In other embodiments, the flowable ECM composition can be sandwiched or otherwise positioned between two substrate layers, and the overall construct dried. One such material is illustrated in FIG. 2, wherein a medical graft material 30 includes first and second substrate (e.g. ECM) layers 32 and 34 sandwiching a fibrous ECM mass layer 36 therebetween. Further, as depicted in FIG. 3, fibrous ECM mass layers 42 and 44 can be provided adherent to a base substrate (e.g. ECM) layer 46 sandwiched therebetween to provide another medical graft construct 40.

The dried cake or mass layer can have any thickness desired. Generally, the thickness of this layer in certain embodiments will be from about 10 microns to about 10 mm, more typically about 0.1 mm to about 5 mm. This dried layer will typically have a more open structure than the underlying base sheet material and will also in advantageous embodiments be less dense and/or less strong under tension than the underlying base or sheet material. Preferred dried cakes or mass will have a somewhat spongy character when dry. Furthermore, the dried cake or mass can be subjected to further processing if desired, including for example cross-linking with any suitable agent such as radiation, chemical agents, or the like. In certain embodiments, treatment to cross-link the cake or layer is not performed (i.e. no additional cross-linking is introduced into the fibrillar mass), and in such embodiments desirable biotropic properties, including angiogenic properties, of the deposited layer can be retained. In other embodiments, cross-linking can be undertaken, but to an extent wherein the deposited cake or mass retains bioactive (e.g. angiogenic) properties. These and other variations in processing of the deposited mass will occur to the skilled artisan in view of the teachings herein.

A variety of techniques for laminating materials, including ECMs, together are known and can be used to prepare multilaminate base substrates. For example, a plurality of (i.e. two or more) layers of collagenous material, for example submucosa-containing or other ECM material, can be bonded together to form a multilaminate structure. Illustratively, two, three, four, five, six, seven, or eight or more collagenous layers containing submucosal or other collagenous ECM materials can be bonded together to provide a multilaminate collagenous substrate material for use in the present invention. In certain embodiments, two to six collagenous, submucosa-containing layers isolated from intestinal tissue of a warm-blooded vertebrate, particularly small intestinal tissue, are bonded together. Porcine-derived small intestinal tissue is preferred for this purpose. The layers of collagenous tissue can be bonded together in any suitable fashion, including dehydrothermal bonding under heated, non-heated or lyophilization conditions, using adhesives, glues or other bonding agents, crosslinking with chemical agents or radiation (including UV radiation), or any combination of these with each other or other suitable methods.

The drying of the deposited gel or other liquid-containing composition to form a dried cake or mass can be conducted in any suitable fashion. Preferably, the drying is conducted by a lyophilization technique, including for example a lyophilization technique involving freeze-drying and/or evaporative cooling. Other drying techniques such as air drying, drying under heated conditions, or vacuum pressing, may also be used to provide all or portion of the drying function.

The materials of the invention can be put to a wide variety of medical uses. These include, for example, use in wound care, hemostasis, tissue support, etc. Advantageously, this material can be used to deliver medical agents, including drugs or other therapeutic or biological agents, in the fibrous mass layer. These substances for delivery may be ionically or covalently linked to components or sorbed therein, as examples.

For the purposes of promoting a further understanding of the present invention and its features and advantages, the following specific experimental is provided. It will be understood that this experimental is illustrative, and not limiting, of the invention.

Example 1

A submucosal gel composition was prepared generally as in U.S. Pat. No. 5,275,826. This gel composition was applied to a submucosa tissue graft sheet material (OASIS wound dressing, Cook Biotech Incorporated, West Lafayette, Ind., USA) to provide a layer thickness of about 1 to 2 mm, and allowed to gel. The resulting construct was dried using lyophilization. The resulting construct provided a strong grafting material including an adherent biotropic fibrous mass of submucosa-derived components on one surface thereof.

The invention claimed is:

1. A dried extracellular matrix graft construct from submucosa tissue, comprising:
   a sheet-form remodelable extracellular matrix substrate layer and an adherent fibrillar mass, said adherent fibrillar mass received directly against said remodelable extracellular matrix substrate layer,
   the adherent fibrillar mass comprising (i) solubilized extracellular matrix components prepared by digesting an extracellular matrix starting material from submucosa tissue with a digestive agent and (ii) an inactivated form of the digestive agent; wherein the native crosslinks present in the extracellular matrix have been disrupted, wherein said extracellular matrix components of said adherent fibrillar mass include collagen, growth factors, glycosaminoglycans, glycoproteins, and proteoglycans retained from the source of submucosa tissue; wherein said adherent fibrillar mass is in the form of a dried layer having a thickness in the range of 10 microns to 10 millimeters; wherein said dried adherent fibrillar mass layer has a density less than that of said underlying base sheet-form remodelable extracellular matrix substrate layer; wherein said components are available in the dried layer for burst release when the dried extracellular matrix graft construct is applied to a wound site, and
   wherein said sheet-form remodelable extracellular matrix substrate layer retains collagen, growth factors, glycosaminoglycans, glycoproteins, and proteoglycans from the submucosa tissue.

2. The medical material of claim 1, wherein the adherent fibrillar mass dried layer exhibits a biotropic character.

3. The material of claim 1, wherein said adherent fibrillar mass dried layer exhibits an angiogenic character.

4. The material of claim 1, wherein said adherent fibrillar mass dried layer comprises bioactive FGF-2, and wherein the digestive agent is an enzyme.

5. The material of claim 1, wherein:
   said one or more growth factors includes one or more members selected from the group consisting of fibroblast growth factor-2, transforming growth factor-beta, vascular endothelial growth factor, epidermal growth factor, and platelet derived growth factor.

6. The material of claim 1, wherein the adherent fibrillar mass dried layer has a spongy character.

7. The material of claim 1, wherein the adherent fibrillar mass dried layer is a lyophilized material.

8. The material of claim 1, wherein said thickness of the adherent fibrillar mass dried layer is in the range of 0.1 millimeters to 5 millimeters.

9. A dried extracellular matrix graft construct from submucosa tissue, comprising:
   a remodelable extracellular matrix sheet material substrate layer and an adherent fibrillar mass received directly against said remodelable extracellular matrix sheet material substrate layer,
   the adherent fibrillar mass comprising (i) solubilized extracellular matrix components prepared by digesting an extracellular matrix starting material from submucosa tissue with a digestive agent and (ii) an inactivated form of the digestive agent; wherein the native crosslinks present in the extracellular matrix have been disrupted, wherein said extracellular matrix components of said adherent fibrillar mass include collagen, growth factors, glycosaminoglycans, glycoproteins, and proteoglycans retained from the source of submucosa tissue; wherein said adherent fibrillar mass is in the form of a dried layer; wherein said dried layer has a density less than that of said underlying base remodelable extracellular matrix sheet material substrate layer; wherein said components are available in the dried layer for burst release when the dried extracellular matrix graft construct is applied to a wound site, and
   wherein said remodelable extracellular matrix sheet material substrate layer includes collagen, growth factors, glycosaminoglycans, glycoproteins, and proteoglycans retained from the source of submucosa tissue.

10. The material of claim 9, wherein said adherent fibrillar mass dried layer comprises randomly deposited collagen fibers.

11. A dried extracellular matrix graft construct from submucosa tissue, comprising:
   a sheet-form biocompatible remodelable extracellular matrix substrate layer, said extracellular matrix substrate layer including collagen, growth factors, glycosaminoglycans, glycoproteins, and proteoglycans retained from submucosa tissue; and an adherent fibrillar mass, wherein said adherent fibrillar mass being prepared by:
(a) digesting an extracellular matrix starting material from submucosa tissue with a digesting agent and inactivating the digesting agent to produce a flowable composition comprising solubilized extracellular matrix components and an inactivated form of the digesting agent,
(b) applying said flowable composition to the sheet-form biocompatible extracellular matrix substrate layer forming a construct, and
(c) drying said construct to provide a dried construct comprising said remodelable extracellular matrix substrate layer and said adherent fibrillar mass; wherein said extracellular matrix components of said adherent fibrillar mass include randomly oriented fibers of collagen, growth factors, glycosaminoglycans, glycoproteins, and proteoglycans retained from submucosa tissue; wherein said adherent fibrillar mass is in the form of a dried layer; wherein said dried adherent fibrillar mass layer has a density less than that of said dried biocompatible extracellular matrix substrate sheet, and wherein said components of said adherent fibrillar mass are available in the dried layer for burst release when the dried extracellular matrix graft construct is applied to a wound site.

12. The medical material of claim 11, wherein the adherent fibrillar mass exhibits a biotropic character.

13. The material of claim 11, wherein said adherent fibrillar mass exhibits an angiogenic character.

* * * * *